United States Patent
DeAngelo

(10) Patent No.: US 8,153,105 B1
(45) Date of Patent: Apr. 10, 2012

(54) SUNBLOCK COMPOSITION WITH PHOTOSTABILIZER AND METHOD OF PREPARATION

(75) Inventor: Gary DeAngelo, Melbourne, FL (US)

(73) Assignee: Sun & Skin Care Research, Inc., Cocoa, FL (US)

( * ) Notice: Subject to any disclaimer, the term of this patent is extended or adjusted under 35 U.S.C. 154(b) by 934 days.

(21) Appl. No.: 12/165,919

(22) Filed: Jul. 1, 2008

Related U.S. Application Data

(60) Provisional application No. 60/947,737, filed on Jul. 3, 2007.

(51) Int. Cl.
- A61K 8/00 (2006.01)
- A61K 8/18 (2006.01)
- A61K 9/00 (2006.01)
- A61Q 17/04 (2006.01)

(52) U.S. Cl. ............. 424/59; 424/401; 424/400; 424/60

(58) Field of Classification Search .................. 424/400, 424/401, 59, 60
See application file for complete search history.

(56) References Cited

U.S. PATENT DOCUMENTS

| | | | |
|---|---|---|---|
| 6,433,025 B1 | 8/2002 | Lorenz | |
| 6,740,312 B2 | 5/2004 | Chopin et al. | |
| 6,787,147 B1 | 9/2004 | Huner et al. | |
| 6,899,866 B2 | 5/2005 | Bonda | |
| 6,962,692 B2 | 11/2005 | Bonda | |
| 7,014,842 B2 * | 3/2006 | Dueva-Koganov et al. | 424/59 |
| 7,108,860 B2 | 9/2006 | Dueva et al. | |
| 7,223,383 B2 | 5/2007 | McNamara | |
| 7,226,582 B2 | 6/2007 | Traynor et al. | |
| 2003/0228267 A1 * | 12/2003 | Aust et al. | 424/59 |
| 2004/0009130 A1 | 1/2004 | Detore et al. | |
| 2004/0121032 A1 | 6/2004 | Epstein et al. | |
| 2004/0228811 A1 | 11/2004 | Krzysik | |
| 2006/0177389 A1 | 8/2006 | Lott | |
| 2006/0210496 A1 | 9/2006 | Mower | |
| 2007/0065378 A1 | 3/2007 | Vondruska et al. | |
| 2010/0111884 A1 * | 5/2010 | Acker et al. | 424/60 |

* cited by examiner

*Primary Examiner* — Johann Richter
*Assistant Examiner* — Luke Karpinski
(74) *Attorney, Agent, or Firm* — Brian S. Steinberger; Joyce Morlin; Law Offices of Brian S. Steinberger, P.A.

(57) ABSTRACT

A sunblock or sunscreen composition with enhanced photostability and a method for preparing and using the novel photostabilizer are provided. The combination of avobenzene, dimethyl capramide, and polyester-8, a copolymer of adipic acid and neopentyl glycol that is terminated with cyanodiphenyl propenoic acid, provides an extra layer of protection to keep the sunscreen working longer to protect the skin from damaging ultraviolet rays, namely, UVA and UVB. Sunblock products with SPF-15 for moderate sun protection. SPF-30 for higher sun protection and SPF-50, specially formulated for fair skin provides high sun protection. The sunblock compositions with the novel photostabilizer have a clean, dry formula that glides on easily for quick absorption, while enlisting sea plant extracts and anti-oxidant vitamins A, C, and E that aid in the reduction of cell damaging free radicals for younger looking skin.

11 Claims, 4 Drawing Sheets

STEP 1: MIX AQUEOUS PHASE INGREDIENTS (Vitamins, Emulsifiers, Thickeners)

STEP 2: ADD DEIONIZED WATER AND AQUEOUS PHASE INGREDIENTS TO MAIN MIXING TANK

STEP 3: MIX OIL PHASE INGREDIENTS (UV Actives, Solvents, Fragrance)

STEP 4: PREPARE PHOTOSTABILIZER

STEP 5: ADD PHOTOSTABILIZER TO OIL PHASE

STEP 6: MIX PHOTOSTABILIZER AND OIL PHASE

STEP 7: ADD OIL PHASE CONTAINING PHOTOSTABILIZER TO AQUEOUS PHASE IN MAIN MIXING TANK

STEP 8: MIX OIL PHASE/PHOTOSTABILIZER/AQUEOUS PHASE

STEP 9: ADD NEUTRALIZER AND MIX ALL COMPONENTS UNTIL HOMOGENEOUSLY BLENDED

STEP 10: REMOVE SUNSCREEN PREPARATION WITH PHOTO STABILIZER FROM MAIN MIXING TANK

Figure 2

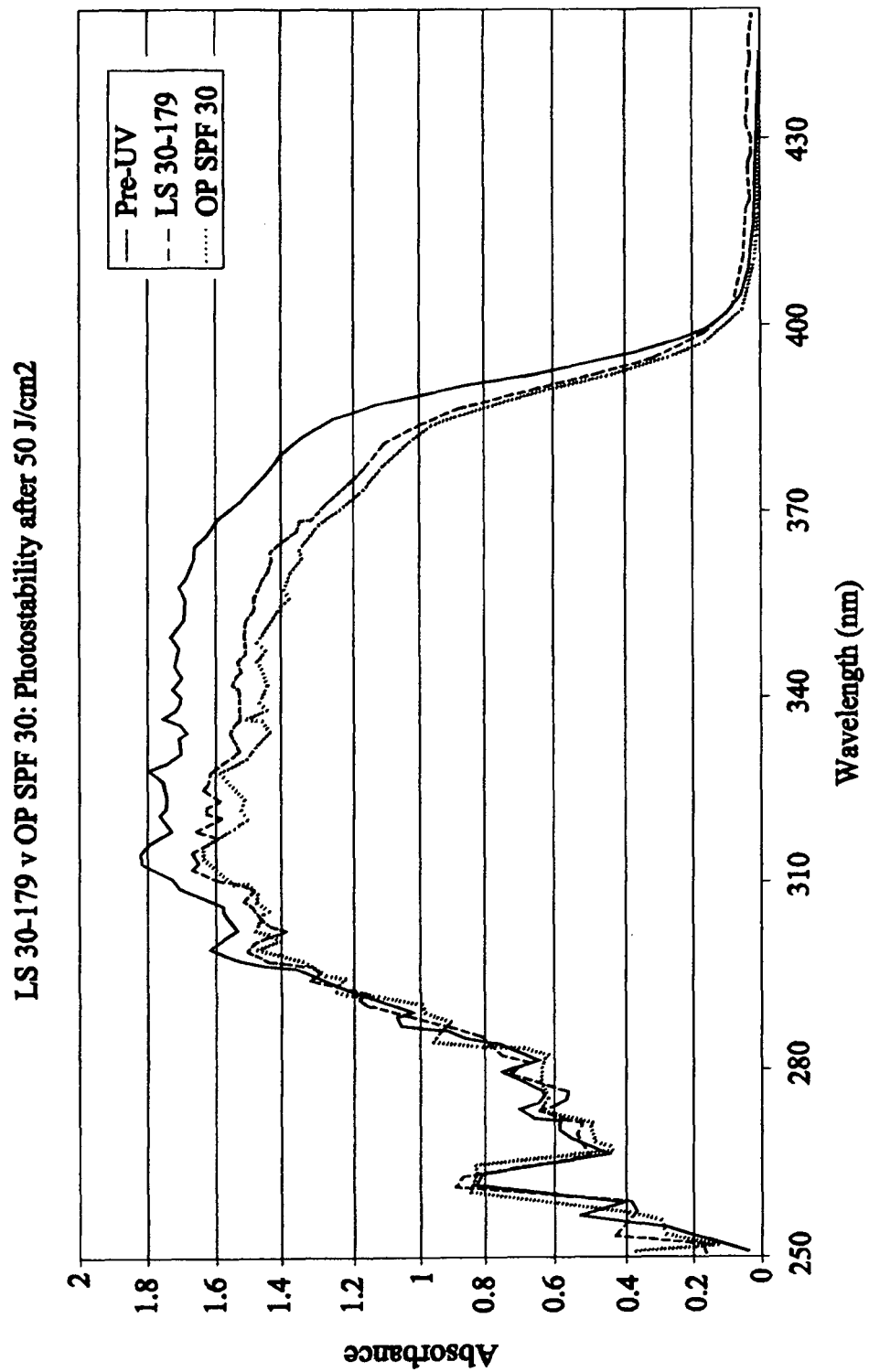

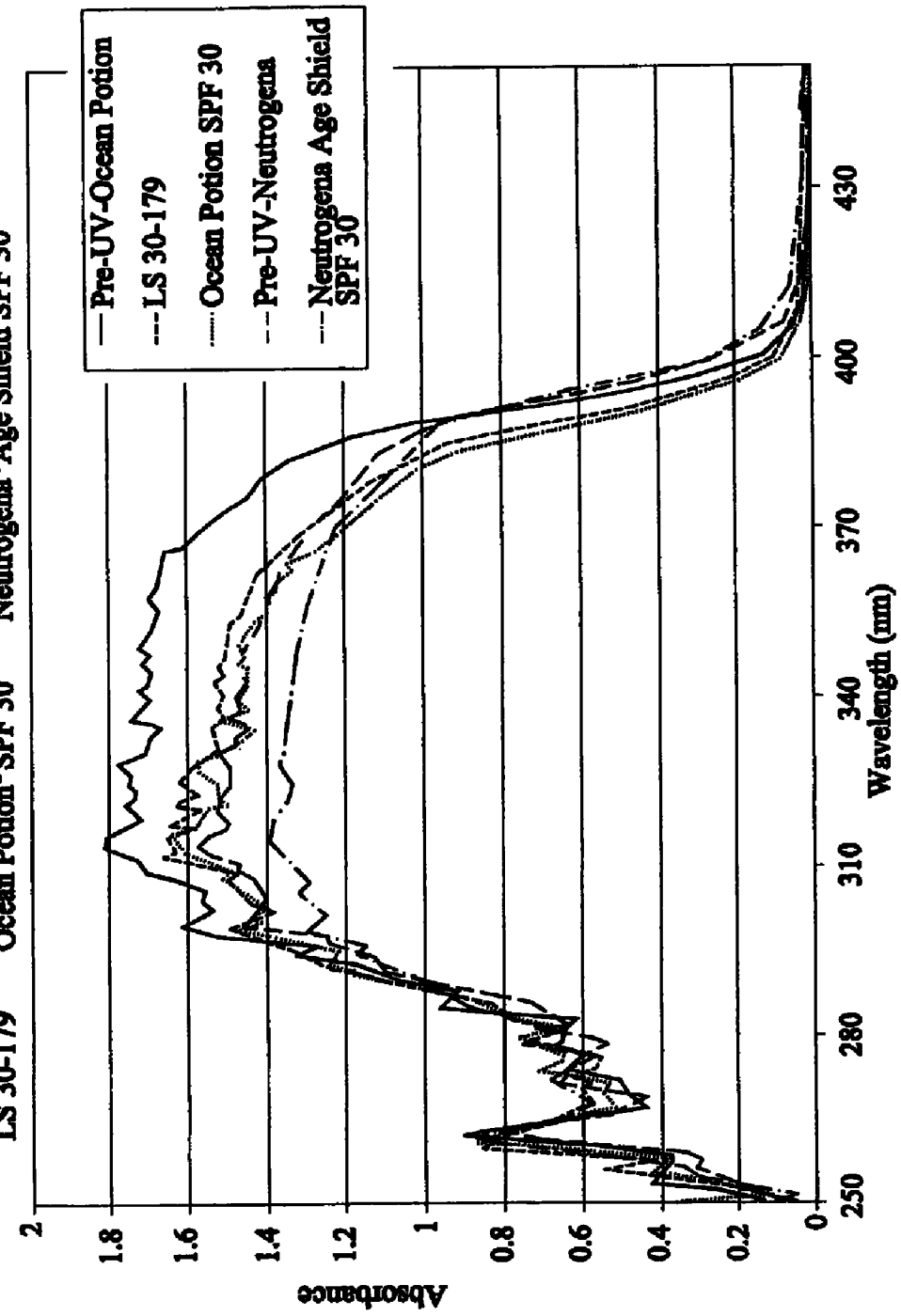

SUNBLOCK COMPOSITION WITH PHOTOSTABILIZER AND METHOD OF PREPARATION

The present application claims the benefit of priority from U.S. Provisional Patent Application Ser. No. 60/947,737 filed on Jul. 3, 2007, which is incorporated herein by reference.

FIELD OF THE INVENTION

The present invention relates generally to sunscreen compositions, and more specifically to, a sunscreen or sunblock formulation with photostability and method for preparing the formulation.

BACKGROUND AND PRIOR ART

Throughout history, the human race has had a special relationship with the sun. Primitive societies in every continent have worshiped the sun as the god that provided warmth and made the crops grow.

Cultures changed over hundreds of years and class systems developed and the sun became a symbol of a different kind, one that clearly defined who you were. Skin color became that visible definer; one that separated working classes from the ruling classes, and separated the master from his servants. Pale skin belonged to the leisure upper classes, while darker skin indicated a life of outdoor labor. The paler the skin the higher the class, and men and women went to great, and sometimes unhealthy, lengths to be pale.

These class distinctions found their way to America, where no Southern belle or Northern society debutante dared go out in the sun without her parasol to protect her delicate pallor. It wasn't until the 20th century that society began accepting bronzed skin.

During the past century, sunscreen compositions have been developed because bronzed skin can be beautiful and sometimes unhealthy, as pale skin was considered to be centuries ago. Sunscreen compositions are applied to the skin to protect the skin from the sun's ultraviolet rays. The formulation, development and marketing of sunscreen compositions are flourishing commercial endeavors today.

Sunlight or ultraviolet radiation in the UV-B range has a wavelength of 290 nm to 320 nm and is known to be the primary cause of erythema, a reddening of the skin known as sunburn. Ultraviolet rays at a wavelength of 320 nm to 400 nm, known as UV-A radiation, produces tanning of the skin, but also lead to skin damage. Prolonged and constant exposure to sunlight or tanning beds may lead to actinic keratoses, carcinomas, premature aging of the skin, skin that is wrinkled, cracked and has decreased elasticity. In other words, prolonged exposure to UV-B and UV-A radiation can get ugly.

Sunscreens have become a necessary commodity and it is alleged that Kurt Vonnegut Jr. advised the 1997 graduating class from Massachusetts Institute of Technology (MIT) "Wear sunscreen. If I could offer you only one tip for the future, sunscreen would be it. The long-term benefits of sunscreen have been proved by scientists, whereas the rest of my advice has no basis more reliable than my own meandering experience . . . . Trust me on the sunscreen."

It is now known that Kurt Vonnegut Jr. did not give the famous speech and advice on wearing sunscreen. It was published on Jun. 1, 1997 and written by Mary Schmich of the Chicago Tribune where she was fantasizing about giving the address. Vonnegut said, "I thought about it and said I didn't think I gave any talk like that, but I wished I had."

Various patents provide the state of the art in sunscreen formulations and even include photostabilizers to provide longer lasting protection. A representative example of patents is discussed below.

U.S. Patent Publ. No. 2007/0065378 to Vondruska et al. discusses SPF 50 formulation of a sunscreen with a water phase premix of ingredients. Sunscreen ingredients include octyl salicylate, polybutene, esters of sorbitol, permulen, other water ingredients disclosed EDTA; quat compounds, fragrance, acrylic copolymer (may be similar to Dermacyl®), Table I lists DI water, carbomer and propylene glycol, hydroxypropyl methylcellulose (methocel), the oil phase includes diisopropanolamine (Dipa), polyisobutene, olive oil, esters sorbitol/polysorbate humectants, triethanolamine, preservatives: methylparaben, propylparaben, ethylparaben, butylparaben, alcoholic solvents include 3-benzophenones.

U.S. Patent Publ. No. 2006/0210496 to Mower discloses a compositon for skin protection from ultraviolet damage that includes homosalate, oxybenzone, seaweed as fucoidan compound combined with radiation protectant titanium oxide; octocrylene, Parsol 1789, avobenzene U.S. Patent Publ. No. 2006/0177389 to Lott discloses a natural sunlight photostable composition and specifically to sunscreen composition containing a triplet combination of avobenzone, octocrylene and oxybenzone to provide and SPF 70 sunscreen that does not appreciably photodegrade.

U.S. Patent Publ. No. 2004/0228811 to Krzysik discusses sunscreen wipes having high sunscreen formulation transfer rate with emphasis on water phase/oil phase and the use of a stabilizing emulsifier.

U.S. Patent Publ. No. 2004/0121032 to Epstein et al. teaches the paragon additive to sunscreen compositions.

U.S. Patent Publ. No. 2004/0009130 to Detore et al. discloses cosmetic compositions with mixture of extracts from yam and soy in comibination with a protective agent. Shows transferring the oil phase to a water phase, includes seaweed extract, dibensoylmethane compounds, benzophenone derivatives, salicylate derivatives, titanium dioxide and the like.

U.S. Pat. No. 7,226,582 to Traynor et al. discloses sunscreen compositions and methods of use in personal care items such as bodywash. Sunscreens with SPF 50 are disclosed that include various compinations of the following ingredients, terphthalic polymers, quaternium compounds, titanium dioxide, octyl salicylate, substituted benzophenones, homosalate, PARSOL 1789, octocrylene, avobenzone, vitamin A, C, D, E, vitamin E acetate. vitamin C palmitate. DERMACRYL, diisopropyl adipate, acrylic/acrylate copolymer, hydroxypropylcellulose, polyethylene terephthalate, disodium EDTA, fragrance components, monoethanolamine, propylene glycol, Carbomer 1382, Ultrez resins, triethanol counter ion and the like. Example 2 shows parasol and octocrylene mixture added to a water phase.

U.S. Pat. No. 7,223,383 to McNamara describes a stabilized sunscreen composition having a particulate inorganic polymer component. The composition is described as an emulsion within a gel.

U.S. Pat. No. 7,108,860 to Dueva et al. discloses sunscreen compositions with sun protection factor (SPF) booster to achieve an SPF of 30.

U.S. Pat. No. 6,899,866 to Bonda teaches combining an oil phase and water phase to obtain a sunscreen. The oil phase may include Dimethyl capramide, Spectrasolv DMDA, RTD, octocrylene with a water phase which contains EDTA salt, carbomer methylpropane diol; also included in the mix is a polyester compound.

U.S. Pat. No. 6,787,147 to Huner et al. discloses a sunscreen composition that contains active sunscreen agents from plants, such as algae and has a SPF of at least 2.

U.S. Pat. No. 6,740,312 to Chopin et al. teaches UV protectant compositions for skin and hair. A combination of ingredients includes titanium oxide particles; the formation of oil/water emulsion using sorbitan emulsifiers, polyester copolymers based on ethylene terephthalate, adipate plasticizer, ascorbic acid, olive oil, thickeners, such as alkyl substituted hydroxyl alkyl cellulose, gelling polymers, carbopol, fragrance, inorganic oxides, and amides of C8-C20 fatty acids.

U.S. Pat. No. 6,433,025 to Lorenz discloses a method for retarding and preventing sunburn by UV light and teaches the use of an algae extract and astaxanthin, which are purported to be more potent than Vitamin E in sunscreen compositions.

U.S. Pat. No. 7,014,842 to Dueva-Koganov et al. and Internet news release, http://money.aol.com/news/articles/a/banana-boatr-sun-cae-products-offer/n2007053116 posted Jun. 11, 2007, disclose a new technology with the trade name AvoTriplex that combines avobenzone, a powerful UVA absorber that, can weaken after prolonged sun exposure, with a stabilizing agent to prevent the sunscreen from breaking down under the sun's rays. The unique combination of ingredients also includes a UVB enhancer. Sunscreen products are provides with an SPF 50.

What is absent in the prior art is a sunscreen photostabilizer having one or more ingredients providing higher sun protection against UVA and UVB sunrays in a clean, dry formula that glides on easily for quick absorption unlike the oily, greasy formulations of the prior art. The present invention fulfills this need.

SUMMARY OF THE INVENTION

The first objective of the present invention is to provide sun screen or sun block protection against UVA and UVB radiation.

The second objective of the present invention is to provide a clean, dry sunscreen formulation that glides easily onto human skin.

The third objective of the present invention is to provide sun screen or sun block protection that includes a formulation with a novel photostabilizer.

The fourth objective of the present invention is to provide a sun screen or sun block potion with a Sunscreen Protection Factor (SPF) of 50 or higher.

The fifth objective of the present invention is to provide a sun screen or sun block potion that is reliable and longer lasting in protecting human skin from harmful ultraviolet radiation from the sun or tanning bed.

A preferred photostabilizer composition for sunscreen or sunblock products includes, a sun blocking agent that absorbs both UVA and UVB rays, a photostabilizer for full spectrum sunscreens, and a polyester; wherein, a preferred sunblocking agent is avobenzone, a preferred photostabilizer for full spectrum sunscreens contains dimethyl capramide and a preferred polyester, polycrylene.

A preferred method for preparing a photostabilizer composition that enhances the photostability of a sunscreen or sunblock composition, includes selecting a mixing vessel, mixing polycrylene in the vessel with a first solvent and a second solvent until the polycrylene has completely dissolved in the first and second solvent, adding the photostabilizer mixture to an oil phase portion of a sunblock composition, and continuing the mixing of the photostabilizer mixture and the oil phase portion of a sunblock composition for an additional period of time of at least 30 minutes. A preferred first solvent is dimethyl capramide (DMDA) and a preferred second solvent is polyisobutene.

A preferred sunscreen composition with photostabilizer includes an aqueous phase, an oil phase, and a photostabilizer containing a polyester, wherein the sunscreen composition is prepared in a cold process in a mixing tank that is operated at atmospheric pressure and room temperature between approximately 65° F. and approximately 85° F.

The preferred sunscreen composition has an aqueous phase that includes Deionized Water, Diisopropyl Adipate, Acrylates Copolymer (Dermacryl AQF), Polyisobutene, Propylene Glycol, Dimethyl Capramide, Triethanolamine (TEA99%), and Algae Extract (Seaweed Extract).

The preferred sunscreen composition has an oil phase that includes Ascorbic Acid, Oleo Europaea (Olive) Fruit Oil, Retinyl Palmitate, Tocopheryl Acetate, Hydroxypropyl Methylcellulose (Methocel), Sorbitan Oleate (Span 80), Acrylates/C10-30AlkylacrylateCross polymer (TR-2), Carbomer (Ultrez 10), Disodium EDTA, Phenoxyethanol+Methyl & Butyl & Ethyl & Propyl & Isobutyl Parabens (Paragon PPM), and Fragrance.

The preferred sunscreen composition has a photostabilizer that includes Avobenzene, dimethyl capramide, and polycrylene. The preferred sunscreen includes a photostabilizer that is separately prepared in a process wherein polycrylene is mixed with a plurality of solvents until the polycrylene is completely dissolved. The preferred plurality of solvents are at least one of polyisobutene and at least one of dimethyl capramide (DMDA) for a combined total of two solvents.

The photostabilizer is added to the oil phase for subsequent mixing with the aqueous phase in the preparation of the final sunscreen composition. The more preferred amount of photostabilizer is present in said composition in an amount from approximately 5.0 weight % to approximately 10.0 weight % based on the total weight of the composition.

Further objects and advantages of this invention will be apparent from the following detailed description of a presently preferred embodiment, which is illustrated in the accompanying drawings.

BRIEF DESCRIPTION OF FIGURES

FIG. 2 shows the steps used to prepare the sunscreen preparation of the present invention.

FIG. 3 is a graph measuring photostability after exposure to 50 J/cm2 for sunscreen compositions LS 30-179 and Ocean Potion SPF 30.

FIG. 4 is a graph measuring photostability after exposure to 50 J/cm2 for sunscreen compositions LS 30-179, Ocean Potion SPF 30 and Neutrogena Age Shield SPF 30.

DESCRIPTION OF THE PREFERRED EMBODIMENT

Figure 1:
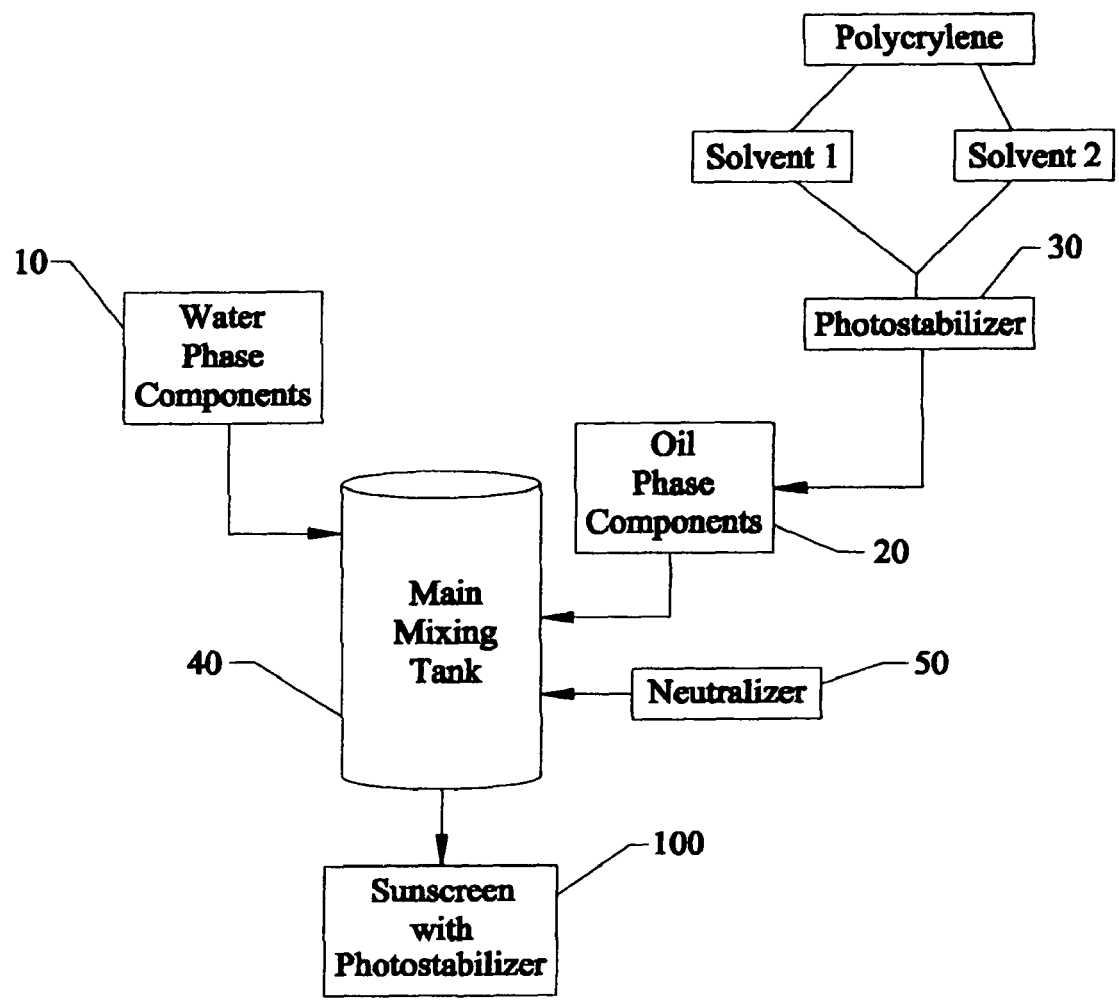
FIG. 1 is a flow chart of the process for preparing the sunscreen preparation of the present invention showing the separate mixing step used to prepare the novel photostabilizer.

Before explaining the disclosed embodiment of the present invention in detail, it is to be understood that the invention is not limited in its application to the details of the particular arrangement shown since the invention is capable of other embodiments. Also, the terminology used herein is for the purpose of description and not of limitation.

It would be useful to discuss the meanings of some words used herein and their applications before discussing the compositions of matter and method of using in a sunscreen or sun block formulation.

"Full-spectrum sunscreen" as used herein means a sunscreen that provides protection from the ultraviolet radiation (UVR) that reaches the Earth's surface, both UV-B (290-320 nm) and UV-A (320 nm-400 nm) protection, ideally through the entire UV-A 1 (340-400 nm) and UV-A 11 (320-340 nm) wavelengths.

"POLYCRYLENE" is a registered trademark owned by CPH Innovations Corporation, Chicago, Ill. The International Nomenclature Cosmetic Ingredient (INCI) name is polyester-8, a copolymer of adipic acid and neopentyl glycol that is terminated with cyanodiphenyl propenoic acid. The chemical name is: hexanedioic acid, polymer with 2,2-dimethyl-1,3-propanediol, 3-[(2-cyano-1-oxo-3,3-diphenyl-2-propenyl) oxy]-2,2-dimethylpropyl 2-octyldodecyl ester. Polycrylene® is referred to herein by the INCI name, polyester-8.

"Sunscreen" as used herein means a preparation, often in the form of a cream or lotion, used to protect the skin from the damaging ultraviolet rays of the sun.

"Sunblock" as used herein means a preparation that prevents sunburn by filtering out the sun's ultraviolet rays, often purported to offer more protection than a sunscreen.

As the definition of a sunscreen and a sunblock preparation appears overlapping, the terms "sunscreen" and "sunblock" are used interchangeably herein. The sunscreen or sunblock preparation of the present invention includes a novel photostabilizer with the trade name SOLAPLEX® is a registered tradename of Sun and Skin Care Research, Inc., a Florida Corporation, 851 Greensboro Road, Cocoa, Fla., the same owner as that of the subject patent application. The formula for the photostabilizer is in Table I below.

TABLE I

| SOLAPLEX ® Formulation | |
|---|---|
| Photostabilizer Ingredients | Weight % of Total Sunblock Formula |
| Avobenzene (Parasol ® 1789) | 2% |
| Polycrylene (Polyester-8) | 2-3% |
| Spectrasolv DMDA (dimethyl capramide) | 1% |

Ingredients for photostabilizer are approximately 5 to approximately 10 weight percent of the total formula, preferably between approximately 5 and 6 weight percent of the total formula.

Table II below provides an example of a sunscreen/sunblock formulation to which the photostabilizer in Table I is added.

TABLE II

| Sunblock formulation for SPF 15 to SPF 50 | |
|---|---|
| SPF Ingredients | Weight % of Total Sunblock Formula |
| Homosalate | 7.5-10% |
| Oxybenzone | 5% |
| Octisalate | 5% |
| Avobenzene (Parasol ® 1789) | 2-3% |
| Octocrylene | 2-2.5% |
| Polycrylene (Polyester-8) | 2-3% |
| Benzophenone-3 | 0.49% |

Ingredients in the sunblock portion of the formulation are approximately 23.99 to approximately 28.99 weight percent of the total formula.

The SPF is adjusted by adding or subtracting Homosalate and Oxybenzone. Adding 2-3% Polycrylene to a sunblock formula with SPF 15, boosts the Persistent Pigment Darkening (PPD) score to 10.5-11 from the usual score of 8+. For photochemical reasons, Benzophenone-3 is added at a concentration less than that required for the EU warning label, and below the concentration at which it functions as a UV filter. The combination of photostabilizer and SPF sunblock ingredients shown in Tables I and II account for from approximately 36 to approximately 43 weight percent of the finished sunblock product.

Table III below provides a list of ingredients that are used to provide a standard sunblock preparation and are used to prepare 100 weight percent of the formulation, which collectively are used in a range of from approximately 57 to approximately 64 weight percent of the total formulation. A person skilled in the art is knowledgeable as to the exact quantities of filler and carrier ingredients that produce the desired sunblock formulation that is commercially marketable and acceptable.

TABLE III

| Sunblock Formulation without SPF Ingredients and Photostabilizer | |
|---|---|
| Ingredient | Function |
| Deionized Water | Aqueous phase |
| Diisopropyl Adipate | Solvent for UV actives |
| Acrylates Copolymer (Dermacryl AQF) | Water Proofer |
| Polyisobutene | Solvent for UV actives |
| Propylene Glycol | Humectant |
| Dimethyl Capramide | Solvent for SOLAPLEX ® complex |
| Polycrylene (Polyester-8) | SOLAPLEX ® UV stabilizer, booster |
| Triethanolamine (TEA 99%) | Neutralizer |
| Algae Extract (Seaweed Extract) | Sea Botanical |
| Ascorbic Acid | Vitamin C |
| Oleo Europaea (Olive) Fruit Oil | Emollient |
| Retinyl Palmitate | Vitamin A |
| Tocopheryl Acetate | Vitamin E Acetate |
| Hydroxypropyl Methylcellulose (Methocel) | Thickener |
| Sorbitan Oleate (Span 80) | Co-emulsifier |
| Acrylates/C10-30AlkylacrylateCross polymer (TR-2) | Thickener, co-emulsifier |
| Carbomer (Ultrez 10) | Thickener |
| Disodium EDTA | Chelating Agent |
| Phenoxyethanol + Methyl & Butyl & Ethyl & Propyl & Isobutyl Parabens (Paragon PPM) | Preservative |
| Fragrance | Aromatic essence |

EXAMPLE 1

Procedure for Mixing the Ingredients in Tables I, II and III

Aqueous phase: Meter in the deionized (DI) water to the main batch tank. Dissolve the Ultrez 10, a carbomer that is commercially available from Noveon, in the DI water for 45-60 minutes. Pre-mix the Methocel E4MP with propylene glycol before adding to the main batch tank. Mix for 15 minutes before adding the following ingredients to the aqueous phase: Disodium EDTA, commercially available from Dow Chemical Company; Vitacon AEM, commercially available from Essential Ingredients; Seaweed Extract, commercially available Medallion Corp.; Dermacyl AQF, commercially available from National Starch; Paragon PPM, commercially available McIntyre Chemical; and Fragrance, commercially available from International Fragrance and Essential Ingredients. Premix the remainder of water phase ingredients and mix until powder is dissolved before adding to the main batch tank: 18.75% of the Octyl Salicylate, commercially available Frutarom; Pemulen TR-2, commercially available from Noveon and Span 80, commercially available from BASF.

Oil phase: In a separate oil tank, add the following UV actives and solvents: the remainder of Octyl Salicylate (81.25%), Homosalate, Octocrylene, DIPA, all of which are commercially available from Frutarom & Essential Ingredients. Begin heating the tank to 120-140 degrees F. It is preferred that the temperature reach at least 120 degrees F. before adding the remainder of the UV actives: Benzophenone-3, Parsol®1789 which are commercially available from Essential Ingredients and DSM Nutritional Products. Parasol® 1789 is a registered trademark of DSM Nutritional Products, Inc. This oil phase mixture must be mixed continuously until the solution is clear, homogenous and free of solids.

Photostabilizer (SOLAPLEX®): In a separate mixing vessel, it is important to premix the following ingredients before adding to the oil tank: Polycrylene, dimethyl capramide (Spectrosolv DMDA), Polyisobutene. After the Polycrylene has completely dissolved in the two different solvents, slowly add to the oil tank of UV actives and mix for an additional 30 minutes.

Add the oil phase containing the photostabilizer mixture to the main batch tank with the aqueous phase with moderate mixing. Mix for 30 minutes before adding triethanolamine (TEA) 99% to neutralize the batch. Mix for a final 90 minutes then take samples from the top and bottom of the batch of sunscreen product for laboratory testing.

FIG. 1 is a flow chart of the procedure for mixing the components of the sunscreen formula of the present invention. Three separate mixing vessels are required; the main batch tank for mixing the aqueous phase ingredients 10, a second vessel for mixing the oil phase ingredients 20, and a third vessel for mixing the photostabilizer 30. The main batch tank 40 is also used to receive and mix the combination of all ingredients, including a neutralizer 50 that is added prior to the last hour and one-half of mixing, to yield the final preparation which is removed as a finished sunscreen preparation with a photostabilizer 100 containing a polyester component.

In FIG. 2, the steps used to prepare the sunscreen preparation 100 of the present invention are listed. In Step 1, aqueous phase ingredients, including thickeners, emulsifiers and skin care agents are pre-mixed. with the deionized water until dissolved. In step 2, deionized water is added to the main mixing tank and additional aqueous phase ingredients, such as, moisturizers, vitamins and the like are premixed and added to the main mixing tank with dissolved aqueous phase ingredients. In step 3, in an oil mixing tank, the oil phase ingredients, including, but not limited to, UV actives and solvents are mixed until the solution is clear, homogenous and free of solids. The oil mixing tank is heated to 120-140° F. while the mixture is continuously stirred.

In step 4, a separate mixing vessel is used to prepare the photostabilizer by adding polycrylene to two solvents, such as polyisobutene and dimethyl capramide (DMDA) and mixing for approximately 30 minutes to form the photostabilizer of the present invention. Step 5 includes adding the photostabilizer slowly to the oil phase ingredients in the oil mixing tank. In Step 6 the oil phase containing photostabilizer is mixed thoroughly, for example, an additional 30 minutes.

Step 7 is adding the oil phase containing photostabilizer to the main mixing tank containing the aqueous phase components. Step 8 is mixing the oil phase with stabilizer and the aqueous phase ingredients for approximately 30 minutes. Then, in Step 9, a neutralizer, such as triethanolamine (TEA), is added before mixing all ingredients to form a homogeneously blended sunscreen mixture. This mixing step is preferably approximately 90 minutes. Step 10 is removing and packaging a sunscreen preparation with photostabilizer.

Referring to FIG. 2, Steps 1, 3 and 4 are preferably prepared as three separate pre-mixes, out of sequence and simultaneously in separate vessels. Each of the three separate pre-mixes is added as directed to the main mixing tank. For example, the aqueous phase ingredients are premixed, then added to the main mixing tank containing deionized water; the oil phase is premixed in an oil mixing tank; the photostabilizer is premixed in a separate vessel before adding to the oil phase mixture in the oil mixing tank. After all premixes are added to the main mixing tank, as directed, a neutralizer is added and all ingredients are mixed for approximately 90 minutes to yield a homogeneously blended sunscreen product.

In summary, the above process is a cold process system that provides photo stability when putting Polyester-8 (polycrylene) along with two different solvents in conjunction with a water soluble water proofing agent. The present system is completed by adding a neutralizer, such as TEA 99% to combine the two phases into one homogenous system.

When following the above procedure and judiciously mixing the ingredients within the ranges provided, an array of sunblock products with SPF-15, SPF-30 and SPF-50 are provided. An anti-aging lotion with SPF-15 provides moderate sun protection against UVA and UVB sunrays. The SPF-15 lotion is for all skin types, it allows gradual tanning without burning. An anti-aging lotion with SPF-30 provides higher sun protection against UVA and UVB sunrays. An anti-aging lotion, specially formulated for fair skin, with SPF-50 provides high sun protection against UVA and UVB sunrays. All of the sunblock products of the present invention have a clean, dry formula that glides on easily for quick absorption, while enlisting sea plant extracts and anti-oxidant vitamins A, C, & E that aid in the reduction of cell damaging free radicals for younger looking skin. The photostabilizer, SOLAPLEX®, enhances the stability of the sunblocking ingredient, avobenzone which makes the sunscreens more reliable and longer lasting as shown in FIGS. 3 and 4. Ultra-violet radiation is simulated using laser energy at 50 joules per centimeter squared (50 J/cm2).

In FIG. 3, a graph of the absorption of ultraviolet radiation of the sunscreen product of the present invention with SPF 30 rating is compared with a competitive product designated LS 30-179. The absorption is plotted against the UV wavelengths between 250 nanometers (nm) and 430 nm. The graph shows greater photostability and less absorbance of UV radiation by the product of the present invention (OP SPF 30) in the wavelength between 310 nm and 370 nm. It was discovered that the addition of polycrylene (Polyester-8) in the formulation of the photostabilizer in the present invention adds an extra layer of protection to keep the sunscreen working properly in sunlight.

FIG. 4 is a graph of the absorption of ultraviolet radiation before and after the application of the sunscreen product of the present invention with SPF 30 rating compared to two competitive products, LS 30-179 and Neutrogena Age Shield SPF 30. The absorption is plotted against the UV wavelengths between 250 nanometers (nm) and 430 nm. The graph shows greater photostability and less absorbance of UV radiation by the product of the present invention (OP SPF 30) than LS 30-179 in the wavelengths between 310 nm and 430 nm. The Neutrogena Age Shield SPF 30 product exhibits greater photostability and less absorbance of UV radiation of products tested in the wavelengths between approximately 285 nm and approximately 370 nm. Then OP SPF 30 of the present invention, performed better than the other two competitive products (LS 30-179 and Neutrogena Age Shield SPF 30) in the wavelengths between 370 nm and 430 nm, the primary source of UV-A radiation that is most damaging to the skin.

In FIGS. 3 and 4, sunscreen photostability was measured in vitro after the application of laser energy in a range of approximately 50 J/cm2. FIG. 4 shows "Neutrogena® Age Shield SPF 30" targeted for protection against premature aging allows less absorption of the harmful UV-A rays in the wavelengths between approximately 310 nm and approximately 400 nm. The versatile sunscreen product of the present invention prevents the absorption of sun burning UVB rays in the wavelength ranges between approximately 250 nm and approximately 310 nm and prevents absorption of skin damaging UVA wavelength ranges from approximately 370 nm to approximately 430 nm, thus providing greater skin protection because there is less absorption of both UVB and UVA rays in the full spectrum of ultraviolet radiation from the sun, in the range from 250 nm to 430 nm. There is also greater photostability than other commercial sunscreen preparations.

While the invention has been described, disclosed, illustrated and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

I claim:

1. A photostabilizer composition for sunscreen or sunblock products consisting of, in combination:
   a sun blocking agent that absorbs both UVA and UVB rays; and
   a photostabilizer for a full UVA and UVB spectrum sunscreen that consists of avobenzone, dimethyl capramide, and polyester-8, a copolymer of adipic acid and neopentyl glycol that is terminated with cyanodiphenyl propenoic acid.

2. A method for preparing a photostabilizer composition that enhances the photostability of a sunscreen or sunblock composition, comprising the steps of:
   a) selecting a mixing vessel;
   b) mixing avobenzone polyester-8, a copolymer of adipic acid and neopentyl glycol that is terminated with cyanodiphenyl propenoic acid, in the vessel with a first solvent and a second solvent until the polyester-8 has completely dissolved in the first and second solvent, wherein said first solvent is dimethyl capramide (DMDA);
   c) adding the mixture of step b) to an oil phase portion of a sunblock composition; and
   d) continuing the mixing of the mixture of step b) and the oil phase portion of a sunblock composition for an additional period of time of approximately 30 minutes.

3. The method of claim 2, wherein the second solvent is polyisobutene.

4. A sunscreen composition with a photostabilizer consisting of:
   an aqueous phase;
   an oil phase; and
   a photostabilizer consisting of avobenzone, dimethyl capramide, and polyester-8, a copolymer of adipic acid and neopentyl glycol that is terminated with cyanodiphenyl propenoic acid, wherein the sunscreen composition is prepared in a cold process in a mixing tank that is operated at atmospheric pressure and room temperature between approximately 65° F. and approximately 85° F.

5. The sunscreen composition of claim 4, wherein the aqueous phase consists of:
   diisoproply adipate;
   acrylates copolymer;
   polyisobutene;
   propylene glycol;
   dimethyl capramide;
   triethanolamine (TEA99%); and
   algae extract (seaweed extract).

6. The sunscreen composition of claim 4, wherein the oil phase consists of:
   ascorbic acid;
   oleo europaea (olive) fruit oil;
   retinyl palmitate;
   tocopheryl acetate;
   hydroxypropyl methylcellulose
   sorbitan oleate;
   acrylates/C10-30 alkylacrylate cross polymer (TR-2);
   carbomer;
   disodium EDTA;
   phenoxyethanol+methyl & butyl & ethyl & propyl & isobutyl parabens; and
   fragrance.

7. The sunscreen composition of claim 4, wherein the photostabilizer consists of:
   avobenzone in an amount that is approximately 2 weight % of the total sunscreen formula;
   dimethyl capramide in an amount that is approximately 1 weight % of the total sunscreen formula; and
   polyester-8, a copolymer of adipic acid and neopentyl glycol that is terminated with cyanodiphenyl propenoic acid in an amount between approximately 2 to approximately 3 weight % of the total sunscreen formula.

8. The sunscreen composition of claim 4, wherein the photostabilizer is separately prepared in a process wherein polyester-8 is mixed with a plurality of solvents until the polyester-8 is completely dissolved.

9. The sunscreen composition of claim 8, wherein the plurality of solvents are at least one of polyisobutene and at least one of dimethyl capramide (DMDA) for a combined total of two solvents.

10. The sunscreen composition of claim 4, wherein the photostabilizer is added to the oil phase for subsequent mixing with the aqueous phase in the preparation of the final sunscreen composition.

11. The sunscreen composition of claim 4, wherein the photostabilizer is present in said composition in an amount from approximately 5.0 weight % to approximately 10.0 weight % based on the total weight of the composition.

* * * * *